(12) United States Patent
Then et al.

(10) Patent No.: US 9,234,851 B2
(45) Date of Patent: Jan. 12, 2016

(54) COLOR MEASUREMENT SYSTEM INCLUDING LATERAL MOVING MEASURMENT CARRIAGE

(71) Applicant: Advanced Vision Technology (A.V.T.) Ltd., Hod Hasharon (IL)

(72) Inventors: Alan Then, Plano, TX (US); Steven Headley, Arlington, TX (US); Mark Rasmussen, Sulphur Springs, TX (US); Rui Xu, Plano, TX (US)

(73) Assignee: Advanced Vision Technology (A. V. T.) Ltd., Hod Hasharon (IL)

( * ) Notice: Subject to any disclaimer, the term of this patent is extended or adjusted under 35 U.S.C. 154(b) by 0 days.

(21) Appl. No.: 14/260,829

(22) Filed: Apr. 24, 2014

(65) Prior Publication Data

US 2014/0320857 A1 Oct. 30, 2014

Related U.S. Application Data

(60) Provisional application No. 61/816,742, filed on Apr. 28, 2013.

(51) Int. Cl.
| | |
|---|---|
| *G01J 3/46* | (2006.01) |
| *G01N 21/86* | (2006.01) |
| *G01J 3/50* | (2006.01) |
| *G01J 3/52* | (2006.01) |
| *G01J 3/02* | (2006.01) |
| *G01N 21/27* | (2006.01) |

(52) U.S. Cl.
CPC .............. *G01N 21/86* (2013.01); *G01J 3/0202* (2013.01); *G01J 3/0237* (2013.01); *G01J 3/50* (2013.01); *G01J 3/02* (2013.01); *G01J 3/46* (2013.01); *G01J 3/524* (2013.01); *G01N 21/27* (2013.01)

(58) Field of Classification Search
CPC ................. G01J 3/02; G01J 3/46; G01J 3/50; G01J 3/51; G01J 3/52; G01J 3/44; G01J 3/534; G01N 21/27
USPC .................................. 356/402–425, 300–334
See application file for complete search history.

(56) References Cited

U.S. PATENT DOCUMENTS

| | | | |
|---|---|---|---|
| 4,003,660 A | 1/1977 | Christie, Jr. et al. | |
| 5,721,618 A * | 2/1998 | Wiklund ................ | G01B 11/00 356/620 |
| 5,818,497 A | 10/1998 | Kerr et al. | |
| 2004/0042022 A1 | 3/2004 | Friedman et al. | |
| 2009/0256087 A1 | 10/2009 | Engler et al. | |

FOREIGN PATENT DOCUMENTS

EP       1 068 958       1/2001

* cited by examiner

*Primary Examiner* — Abdullahi Nur
(74) *Attorney, Agent, or Firm* — Merchant & Gould P.C.

(57) ABSTRACT

A color measurement system laterally determines chromatic characteristics of a printed substrate. A measurement carriage includes a measurement head for laterally moving across the printed substrate and a measurement magnetic coupler slidably mounts onto a measurement rail positioned on a first side of the printed substrate. A backing carriage includes backing surface(s) and backing magnetic coupler(s). Each backing magnetic coupler is associated with a respective backing surface. Each backing magnetic coupler can be coupled with the measurement magnetic coupler for coupling the measurement carriage with the backing carriage. The backing carriage slidably mounts onto a backing rail positioned on a second opposite side of the printed substrate. The measurement carriage or backing carriage includes a motor for moving across a respective measurement rail or backing rail. Another measurement carriage and backing carriage move across another measurement rail and backing rail by coupling with the first measurement carriage and backing carriage.

6 Claims, 3 Drawing Sheets

COLOR MEASUREMENT SYSTEM INCLUDING LATERAL MOVING MEASURMENT CARRIAGE

This application claims benefit of U.S. Provisional Ser. No. 61/816,742, filed 28 Apr. 2013 and which application is incorporated herein by reference. To the extent appropriate, a claim of priority is made to the above disclosed application.

FIELD OF THE INVENTION

The disclosed technique relates to inspection of printed material, in general, and to methods and systems for laterally moving across a printed material for acquiring spectral measurements thereof, in particular.

BACKGROUND OF THE INVENTION

Spectral measurements of objects are required by various industries for different applications. The term 'object' herein refers to continuous printed substrates or discrete objects such as packages, fruits, vegetables, plastic toys, boxes and the like. For example, in the food industry, spectral measurements are used for sorting and quality control. In the biological materials industry, spectral measurements are used for the examination of dye markers absorbed by various cells or organisms, or to non-invasively identify pigments in a single cell or clusters of cells and to map the spatial organization of phototrophic groups in complex microbial communities. In the chemical industry, spectral measurements are used, for example, to identify the presence of pollutants in the air, by distinguishing the pollutants from the nitrogen, oxygen, water and other expected constituents.

In particular, spectral measurements are used in the printing industry for determining chromatic characteristics of objects. The chromatic characteristics may be represented, for example, by the estimated coordinates of a printed color in a color space (e.g., CIEXYZ, CIELUV, CIELAB, RGB, CYMK, HIS and the like), determined according to measurements of the light, which is either reflected from or transmitted through the object. The chromatic characteristics may further relate to the optical reflection densities of the inks deposited on a printed substrate or an object. The chromatic characteristics may also relate to the spectral composition of the light reflected from the printed substrate.

Objects, which at least a portion thereof, transmit at least a portion of incident light thereon, are herein referred to collectively as non-opaque objects. The term 'non-opaque' is defined, for example, in accordance with the ISO 13655 standard, where "opaque" is defined as a material with opacity greater than 99. A material behind the non-opaque objects may affect the reflectance factor of light impinging on the non-opaque objects. Alternatively, the material behind the non-opaque objects may affect the transmittance factor of light illuminating the non-opaque objects. When spectral measurements are made, the material behind the non-opaque object is referred to herein as a 'backing.' The reflectance factor can be defined as the ratio of light reflected from the object to light reflected from a perfect reflecting diffuser, both illuminated with the same light from the same direction. Similarly, the transmittance factor can be defined as the ratio of light transmitted through the object to light transmitted through a perfect transmitting diffuser, both illuminated with the same light from the same direction. The reflectance or transmittance factors may in turn affect the estimation of chromatic characteristics of the non-opaque objects, which are determined according thereto. For example, the reflectance factor is used when determining the X, Y and Z tristimulus values (e.g., according to the CIE 1931 XYZ color space) according to spectral measurements of the reflected light from the non-opaque object. Thus, for example, the determined X, Y and Z tristimulus values of a green color printed on a non-opaque material with a shiny aluminum backing will be different than the determined X, Y and Z tristimulus values of the same green color printed on the same non-opaque material with a white material backing.

To achieve repeatability and reproducibility of measurements of chromatic characteristics from a non-opaque object, as well as to provide a basis for comparing measurements between different measurement systems, a standard backing may be placed behind the non-opaque object during spectral measurements. During such spectral measurements, the printed material may need to be in proximate contact with the backing. The term 'repeatability of measurement' relates herein to a measurement of a sample, which can be repeated (i.e., for that same sample), with the same measuring instrument, under substantially the same measurement conditions, with substantially the same results (i.e., within a determined tolerance). The 'reproducibility of measurement' relates herein to a measurement of a sample, performed by an observer, with a measurement instrument, under specified measurement conditions, which can be reproduced by another observer, with substantially the same measurement instrument, under substantially the same measurement conditions, with substantially the same results (i.e., within a determined tolerance). For example, according to the ISO 13655 standard, the backing may be black, referred to as a black backing, or white, referred to as a white backing. Specifically, Annex A of the ISO 13655 standard defines the requirements of the white and black backings. The ISO 13655 standard further recommends that the measurements of light reflected off the non-opaque object, placed on and in contact with the backing, should be corrected relative to the reflection measurements of the backing alone. Similarly, other standards and industry accepted specifications such as those provided by the American Society for Testing and Materials (ASTM), the American National Standards Institute (ANSI), the Deutsches Institut für Normung (DIN), Fogra, and the Flexographic Technical Association (FTA), have various existing and evolving standards and specifications for colorimetric measurements. Such standards and specifications are, for example, FIRST, SNAP, Specifications Web Offset Publications (SWOP), General Requirements for Applications in Commercial Offset Lithography (GRACOL) and the like.

Systems and methods for the measurement of chromatic characteristics of non-opaque objects are known in the art. U.S. Pat. No. 5,047,652 issued to Lisnyansky, et al., and entitled "System for On-line Measurement of Color, Opacity and Reflectance of a Translucent Moving Web", is directed to a system for on-line optical measurement of properties of a translucent moving web. The translucent moving web is conveyed on a backing roll. The backing roll has a surface which includes at least two portions respectively comprising the "white" and "black" optical standards. For example, one semi-cylindrical half of the backing roll surface comprises the "white" optical standard, and the other semi-cylindrical half of the roll surface comprises the "black" optical standard. The backing roll is positioned such that a circumferential portion of the roll surface contacts the back web surface where the web characteristic is to be optically measured. For measuring web characteristics, an optical sensing device is positioned adjacent the circumferential portion of the roll surface so as to view the front web surface backed by the one or more optical standards of the surface. The optical sensing device includes a scanning mounting operable to traverse in a direction parallel to the roll axis such that measurements can be made across the width of the web.

U.S. Pat. No. 5,818,497 issued to Kerr, et al., and entitled "Apparatus for Magnetically Coupling a Lead Screw to a Print Head", is directed to an apparatus for coupling a lead screw to a print head. The print head is mounted on a movable translation stage member which, is supported for low friction slidable movement on translation bearing rods. The movable translation stage is magnetically coupled with a drive nut of a lead screw by a magnetic assembly. The lead screw includes an elongated, threaded shaft which is attached to a linear drive motor on its drive end. It is noted that rotation of the drive nut typically produces undesirable movement of the translation stage member. The magnetic assembly functions to provide a rotational constraint to the drive nut for consequently preventing the undesirable movement.

US Patent Application Publication No. 2009/0256087 to Engler Hans, et al., entitled "Measuring Apparatus Having a Movable Measuring Device in a Press" is directed to a measuring apparatus for scanning moving sheet-like printing materials. The scanned printed sheets are transported through a sheet transport section by transport cylinders. A measuring device is disposed above the sheet transport section. The measuring device has a movable runner, which carries the measuring optics. The linear drive moves the measuring optics concomitantly in parallel in the sheet transport direction during the measuring operation, so that the time of the measuring operation can be prolonged. During the measuring operation, the printed sheet can additionally be supported by a tray-like measuring support, in order to keep the distance between measuring device and printed sheet constant. The measuring support is moved concomitantly with the sheet and is additionally designed to be vertically adjustable by means of an adjusting element, so that the distance between printed sheet and measuring device can be regulated.

U.S. Pat. No. 4,003,660 to Christie, Jr., et al., entitled "Sensing Head Assembly for Multi-Color Printing Press Online Densitometer" is directed to a sensing head assembly for multi-color printing press online densitometer. The sensing head assembly is moved across the width of the scanned web by a reversible electric motor driving a reversible rotating drive screw.

US Patent Application Publication No. 2004/0042022 to Friedman, Michael et al., entitled "Active Color Control for a Printing Press" is directed to a system for the accurate measurement and control of image color density on an operating printing press. The color control system scans a conveyed web. The color control system includes an imaging assembly including a CCD digital camera and a strobe light. The imaging assembly scans the top side of the web. Another imaging assembly including another CCD digital camera and another strobe light scans the bottom side of the web. Each imaging assembly is mounted on a respective carriage, which moves and positions the camera and strobe at an operator specified location across the web width.

European Patent No. EP 1 068 958, issued to Kerr, Roger Stanley and entitled "Method and apparatus for positioning a writing assembly of an image processing apparatus" is directed to an image processing apparatus including an imaging drum, and a print head. The print head is driven by a lead screw and stepper motor for moving along a line parallel to a longitudinal axis of the imaging drum as the imaging drum rotates.

SUMMARY OF THE INVENTION

It is an object of the disclosed technique to provide a novel system for laterally transiting a measurement carriage and a backing carriage, in unison, across the width of a printed substrate, for determining the chromatic characteristics of the printed substrate. In accordance with the disclosed technique, there is thus provided a color measurement system for laterally determining the chromatic characteristics of a printed substrate conveyed by a conveying apparatus, the system including a measurement carriage and a backing carriage, the measurement carriage including a measurement head for laterally moving across the width of the printed substrate and a measurement magnetic coupler, the measurement carriage slidably is mounted onto a measurement rail positioned on a first side of the printed substrate, the backing carriage including at least one backing surface and at least one backing magnetic coupler, each of the at least one backing magnetic coupler is associated with a respective one of the backing surface, each of the at least one backing magnetic coupler can be coupled with the measurement magnetic coupler for coupling the measurement carriage with the backing carriage, the backing carriage is slidably mounted onto a backing rail positioned on a second side of the printed substrate, opposite the first side, wherein a selected one of the measurement carriage and the backing carriage including a motor for moving across a respective one of the measurement rail and the backing rail, and wherein another one of the measurement carriage and the backing carriage is moved across another one of the measurement rail and the backing rail by is coupled with the first one of the measurement carriage and the backing carriage.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1B:
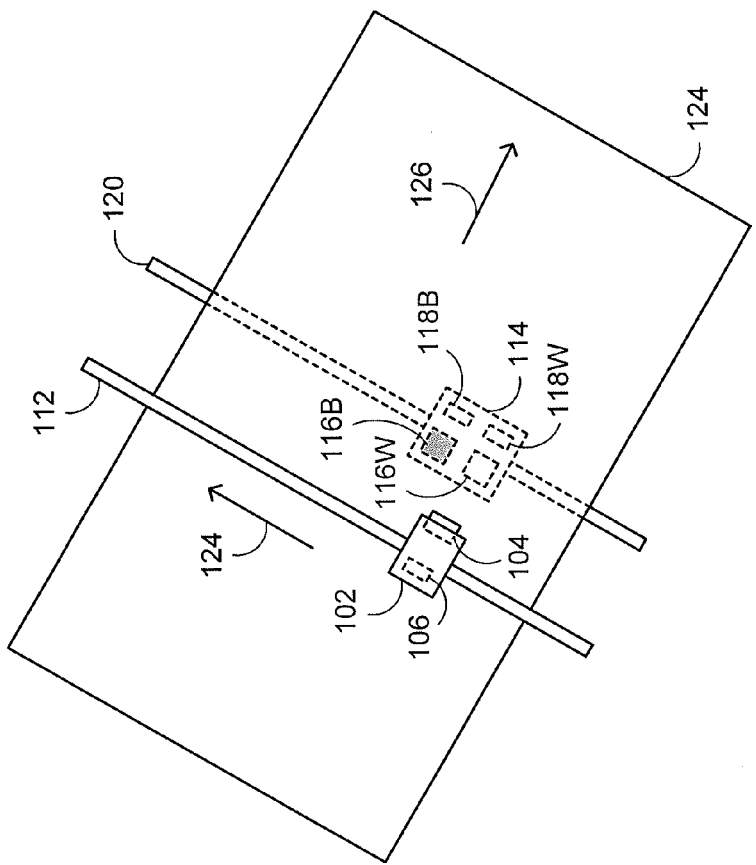
FIGS. 1A and 1B are schematic illustrations of a system, for laterally moving across a printed web for acquiring color measurements of the web, constructed and operative in accordance with an embodiment of the disclosed technique.

The disclosed technique overcomes the disadvantages of the prior art by providing a color measurement system for determining the chromatic characteristics of objects conveyed by a conveying apparatus. The color measurement system laterally moves across the width of the conveyed object for acquiring color measurements. The color measurement system includes a mobile measurement carriage, including a measuring head (e.g., a spectrophotometer, densitometer, colorimeter) and a mobile backing carriage, including a backing surface. Each of the measurement carriage and the backing carriage is mounted on a respective lateral rail, on opposite sides of the conveyed objects (e.g., the measurement carriage rail is above the conveyed object and the backing carriage is below). The measurement and the backing carriages move in unison, laterally across the width of the conveyed objects for acquiring color measurements of the conveyed objects. In this manner, the measurement head is maintained over the backing surface throughout the lateral travels of both carriages. In other words, the relative position between the measurement head and the backing surface is maintained, or changes in the relative position between the measurement head and the backing surface are controlled.

The conveying apparatus conveys objects that include non-opaque portions, and which are transported over in a production line. The term 'production line' refers herein to a line of machines which transform the state (e.g., color, shape, ascription and the like) of an object. Such machines are, for example, printing machines, coloring machines, sorting machines, impression machines, various packaging and converting machines and the like. The machines are connected by the conveying apparatus, which transports the objects along the production line.

The backing surface exhibits specific known chromatic characteristics such as spectral reflectance, lightness, chroma, hue, XYZ tristimulus values and any other chromatic characteristics which can be determined from the spectral reflectance, or optical characteristics, such as refractivity, diffusivity, fluorescence, and opacity, which conform to a given standard, or are intended for specific measurement conditions. The backing surface may be a plate made of, or coated with a material exhibiting the aforementioned specific optical or chromatic characteristics. The aforementioned specific surface characteristics may be specified by an international standard such as the ISO 13655 standard, or be designed to meet the needs of a specific combination of object characteristics and required measurement conditions. These measurement conditions may be lighting characteristics (e.g., intensity, spectral composition and the like), optical detector position and the like. For example, ink film thickness is measured using optical reflection densities (i.e., the logarithm to base ten of the ratio between the intensity of the light incident on the printed ink film and the intensity of the light reflected from the ink film). When measuring ink film thickness on a double-sided printed substrate, the substrate is placed on a black backing. Thus, inked areas on the non-inspected side do not significantly influence the measurements of the ink film thickness on the inspected side of the substrate.

Figure 1A:
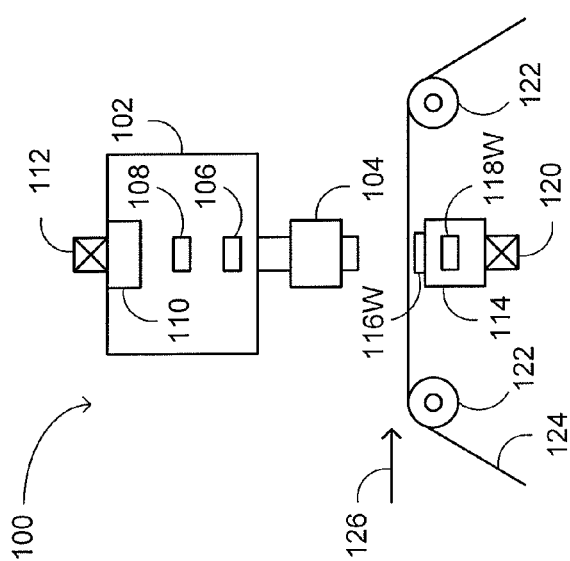

Reference is now made to FIGS. 1A and 1B, which are schematic illustrations of a system, generally referenced 100, for laterally moving across a printed web for acquiring color measurements of the web, constructed and operative in accordance with an embodiment of the disclosed technique. Color measurement system 100 includes a measurement carriage 102 slidably mounted on a measurement rail 112, and a backing carriage 114 slidably mounted onto a backing rail 120. Measurement carriage 102 includes a measurement head 104, a measurement magnetic coupler 106, a control unit 108 and a motor 110. Control unit 108 is coupled with measurement head 104, measurement magnetic coupler 106, and with motor 110 for controlling the operation of each. Backing carriage 114 includes a white backing surface 116W, a black backing surface 116B, a white magnetic coupler 118W, and a black magnetic coupler 118B.

Each of measurement carriage 102 and backing carriage 114 is slidably moved along low friction rails 112 and 120, respectively. In particular, measurement carriage 102 and backing carriage 114 are moving in unison, such that the relative position between measurement head 104 and backing surfaces 116W and 116B is maintained or controlled. For moving the carriages in unison, measurement carriage 102 is coupled with backing carriage 114 via the magnetic couplers thereof. Thereby, when motor 110 displaces measurement carriage 102 over measurement rail 112, measurement magnetic coupler 106 'pulls' one of white magnetic coupler 118W or black magnetic coupler 118B causing backing carriage 114 to slide over backing rail 120.

Measurement magnetic coupler 106 is coupled with either one of white magnetic coupler 118W or black magnetic coupler 118B, and can decouple from the magnetic coupler it is currently coupled with and couple with the other magnetic coupler. For example, measurement magnetic coupler 106 can be coupled with black magnetic coupler 118B, decouple therefrom, and couple with white magnetic coupler 118W.

As described above, the coupling of measurement carriage 102 with backing carriage 114, enables employing a single motor for displacing both carriages. In addition, the relative position between the carriages is strictly maintained or controlled. In this manner, measurement head 104 is maintained optically coupled with one of backing surfaces 116W and 116B throughout the lateral displacements of the carriages across the width of the conveyed printed web (depending on which of magnetic couplers 118W and 118B is coupled with measurement magnetic coupler 106).

A conveying apparatus (not referenced), including two conveying rollers 122, conveys a non-opaque object 124 such as a non-opaque printed web, for example, from a printing press to a cutting machine (both not shown). Printed web 124 (also referred to herein below as printed substrate) is made of, for example, paper, a flexible polymer, plastic, metal or a laminate of at least two materials. Printed web 124 moves in the direction indicated by an arrow 126 (i.e., conveyance direction 126) over rollers 122.

Each of measurement carriage 102 and backing carriage 114 travels on an opposite side of printed web 124. For example measurement carriage 102 travels above printed web 124 (i.e., facing the front printed side of printed web) and backing carriage 114 travels below (i.e., facing the back side of printed web 124, which may or may not be printed).

As printed web 124 is rolled over backing surfaces 116W and 116B, printed web 124 comes in proximate contact with the backing surfaces, and measurement head 104 can acquire color measurements (or otherwise optically inspect) printed web 124. Measurement head 104 includes an optical detector (e.g., a spectrophotometer, a hyperspectral imager, a densitometer or a color camera, such as a line or area color camera employing a standard color space such as the CIE XYZ or RGB) and a light source (both not shown).

The light source illuminates printed substrate 124 and one of backing surfaces 116W or 116B (depending on which one is currently coupled with measurement head) with a standard light. The standard light can be, for example, the CIE D65 illuminant, the CIE D50 illuminant, the CIE A illuminant, and the like. The light emitted by the light source is transmitted through non-opaque printed web 124, and is reflected from (i.e., either specularly or diffusely) the respective backing surface back through non-opaque printed web 124 to the detector. In other words, the light emitted by the light source optically interacts with both the non-opaque printed web and the backing surface. The optical detector receives the reflected light and acquires information at least relating to the chromatic characteristics of printed web 124 as influenced by the backing material. Thus when using the same backing surfaces for different chromatic measurements, chromatic characteristics of printed web 124 acquired by different optical detectors will only differ due to the differences in the optical detectors and light sources used. Alternatively, the light source is not mounted onto measurement carriage 102 and instead is supported by a light source supporter (not shown), which can also be coupled with measurement magnetic coupler 106 for following measurement carriage 102, such that the relative position between the light source and measurement head 104 is maintained.

Each of white backing surface 116W and black backing surface 116B is made of, or is coated with, a material exhibiting specific determined chromatic characteristics (e.g., spectral reflectance, lightness, chroma and hue) and optical characteristics (e.g., refractivity, diffusivity, fluorescence and opacity). For example, backing surfaces 116W and 116B may be made of, or coated with, a white material, which complies with the backing characteristics specified in Annex A of the ISO 13655 standard. Black and white backing surfaces 116B and 116W are relatively small (i.e., the width thereof occupies only a portion of the width of printed substrate 124), therefore the amount of required backing material is reduced. In addition black and white backing surfaces 116B and 116W can be easily replaced as they are mounted on a carriage which is separate from the conveying apparatus.

It is recognized by those skilled in the art that the backing material need not be restricted solely to white backing or black backing, and that backing consisting of various colors may be desirable given the specifics of a given measurement. That is, the backing material can have any desired spectral properties to better achieve the reproducibility and repeatability of measurement.

In the example set forth in FIGS. 1A and 1B, there are two backing surfaces, each associated with a respective magnetic coupler. Alternatively, the backing carriage includes a different number of backing surfaces and respective backing magnetic couplers. For example, the backing carriage includes only a white backing surface and a single magnetic coupler, or includes three different backing surfaces, each associated with a respective magnetic coupler.

Each of measurement magnetic coupler 106 and black and white magnetic couplers 118B and 118W, can be, for example, a magnet, a magnetic material (e.g., paramagnetic or ferromagnetic), or an electromagnet. The magnetic couplers enable remotely coupling measurement carriage 102 with backing carriage 114, without physically connecting them. Thereby, the relative positions of the carriages, and in particular the relative position of measurement head 104 and backing surfaces 116B and 116W are coordinated (e.g., maintained or controlled). Additionally, magnetic coupling enables easily decoupling and re-coupling of measurement magnetic coupler 106 and either one of black and white magnetic couplers 118B and 118W.

In accordance with an alternative embodiment of the disclosed technique, the backing carriage is motorized and controlled, and the measurement carriage is following it, by being magnetically coupled thereto. In accordance with another alternative embodiment of the disclosed technique both the measurement carriage and the backing carriage are both motorized and controlled and the respective controllers coordinate the relative position between the measurement and the backing carriages and maintain the measurement head optically coupled with the backing surfaces.

In accordance with yet a further alternative embodiment of the disclosed technique, in a transmission type measurement, the backing carriage is replaced by a lighting carriage including a light source. A non-opaque backing surface is positioned on the measurement carriage between the measured object and the light detector.

Reference is now made to FIGS. 2A, 2B, 2C and 2D, which are schematic illustrations of a color measurement system, generally referenced 200, for laterally moving across a printed web for acquiring color measurements of the web, constructed and operative in accordance with another embodiment of the disclosed technique. FIGS. 2A, 2B, 2C and 2D are depicted from a front perspective, such that a printed substrate 212 is conveyed in a direction perpendicularly extending from the image plane toward (or away from) the viewer. Color measurement system 200 includes a measurement carriage 202 mounted on a measurement rail 204, and a backing carriage 206 mounted on a backing rail 210. Measurement carriage is substantially similar to measurement carriage 102 of FIGS. 1A and 1B, and includes a measurement head, a controller, a motor, and a measurement magnetic coupler (all not shown). Backing carriage 206 is substantially similar to backing carriage 114 of FIGS. 1A and 1B, and includes a black backing surface 208B, a white backing surface 208W, and a black and a white magnetic couplers (both not shown).

Figure 2A:
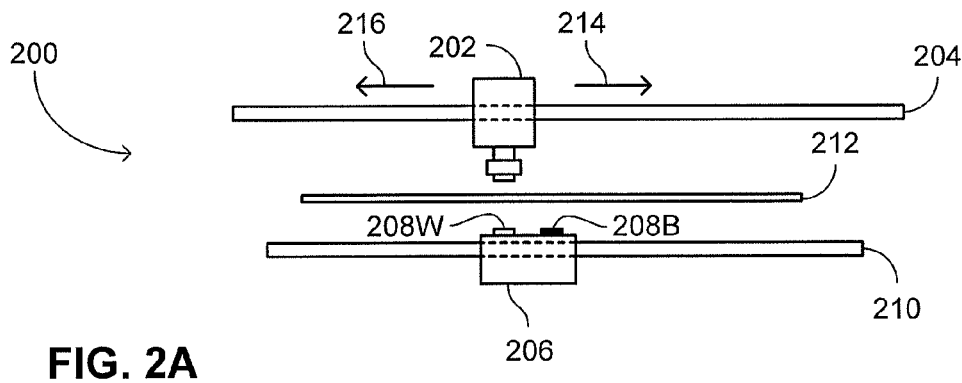
FIGS. 2A, 2B, 2C and 2D are schematic illustrations of a color measurement system, for laterally moving across a printed web for acquiring color measurements of the web, constructed and operative in accordance with another embodiment of the disclosed technique.

With reference to FIG. 2A, backing carriage 202 can be laterally transited in the direction of arrows 214 and 216, for acquiring color measurements (or otherwise optically inspecting) printed substrate 212. In the example set forth in FIG. 2A, the magnetic coupler of measurement carriage 202 is coupled with the white magnetic coupler of backing carriage 206. Thus, backing carriage 206 follows measurement carriage 202, such that the measurement head is optically coupled with white backing surface 208W. That is, the relative position between the measurement head and white backing surface 208W is maintained via the magnetic couplers. In this manner, for example, the light source illumination impinges on the same spot of white backing surface 208W, throughout the measurement process. In a similar manner, when the magnetic coupler of measurement carriage 202 is coupled with the black magnetic coupler of backing carriage 206, the optical detector receives light reflected from the same spot of black backing surface 208B, throughout the measurement process. Thus, by coupling measurement carriage 202 with backing carriage 206, measurement system 200 avoids the problem of potential non-uniformity (i.e., variance) of the backing surface. For example, a backing surface which extends across the width of the substrate might exhibit variance in the chromatic characteristics thereof between different areas thereof, due to wear and tear or imperfect production or coating process. In accordance with the disclosed technique, the same spot of the backing surfaces is employed throughout the measurement process, and therefore the reproducibility of the measurement conditions is enhanced. Additionally, black and white backing surfaces 208B and 208W are relatively small (i.e., the width thereof occupies only a portion of the width of the printed substrate). Therefore, the characteristics of the backing surface are substantially uniform which further enhances the reproducibility of the measurement conditions.

Figure 2B:
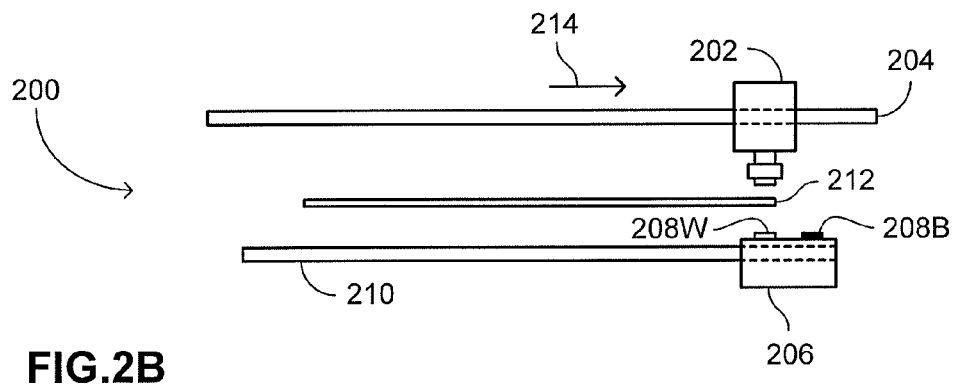

With reference to FIG. 2B, the magnetic coupler of measurement carriage 202 is coupled with the white magnetic coupler of backing carriage 206. Measurement carriage 202 and backing carriage 206 travel in unison toward the right hand side of printed substrate 212 (i.e., in the direction of arrow 214). After completing the movement toward the right hand side of printed substrate 212, the measurement head of measurement carriage 202 is positioned above the right hand side end of printed substrate 212, as depicted in FIG. 2B.

As can be seen in FIG. 2B, both measurement rail 204 and backing rail 210 extend beyond the side ends of printed substrate 212, for enabling backing surfaces 208B and 208W to back the full width of printed substrate 212. Additionally, measurement carriage 202 can travel greater distances over measurement rail 210, than backing carriage 206 can over backing rail. In particular, measurement carriage 202 can extend beyond both ends of printed substrate 212, while white backing surface 208W cannot travel beyond the right end of printed substrate 212 and black backing surface 208B cannot travel beyond the left end of printed substrate 212. Thus, when backing carriage 206 is stopped at the right end of rail 210, measurement carriage 202 can continue traveling in the direction of arrow 214. Thereby, the magnetic coupler of measurement carriage 202 is decoupled from the white magnetic coupler of backing carriage 206.

Figure 2C:
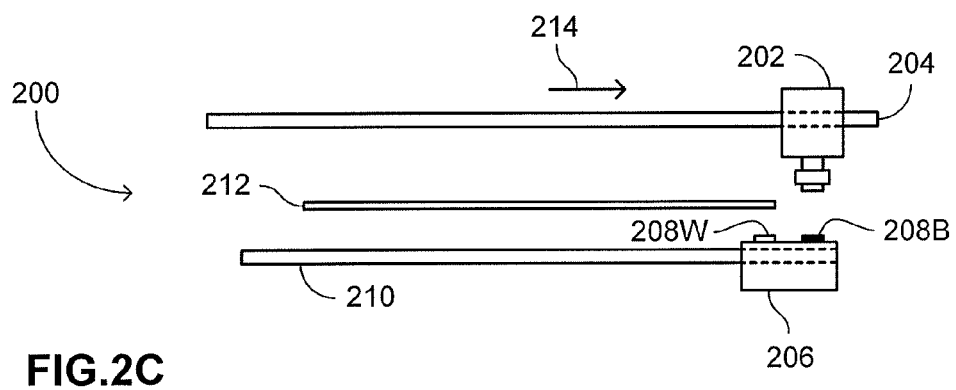

With reference to FIG. 2C, the magnetic coupler of measurement carriage 202 is no longer coupled with the white magnetic coupler (208W) of backing carriage 206, but instead coupled with the black magnetic coupler (208B). As mentioned above, when measurement carriage 202 continues traveling in the direction of arrow 214 after backing carriage 206 is stopped at the right end of backing rail 210, the magnetic coupler of measurement carriage 202 is decoupled from the white magnetic coupler of backing carriage 206, and becomes coupled with the black magnetic coupler of backing carriage 206. Thereby, measurement system 200 switches from a white backing measurement mode to a black backing measurement mode, as depicted in FIG. 2C. Once the measurement head acquired color measurements of printed substrate 212 from the left end to the right end, across its entire width, measurement carriage 202 is decoupled from the white magnetic coupler and is coupled to the black one. Then, measurement carriage 202 is transited in the direction of arrow 216 (i.e., to the left hand side) and backing carriage 206, coupled thereto via the black magnetic coupler, is moving in unison. Thereby, measurement system 200 acquires measurements across the width of printed substrate 212 from the right end to the left end with a black backing surface.

Figure 2D:
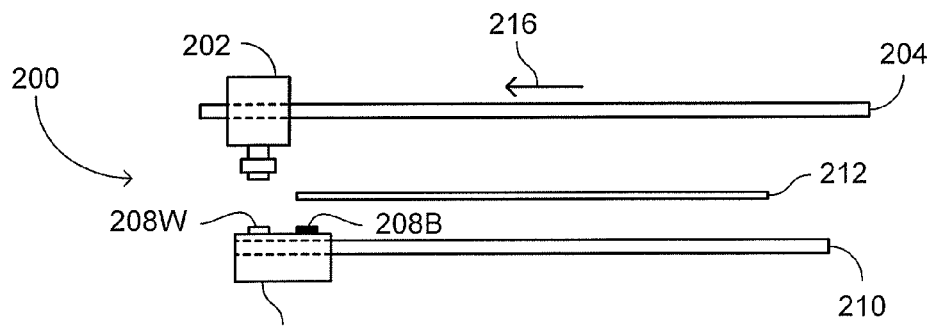

With reference to FIG. 2D, the magnetic coupler of measurement carriage 202 is coupled with the black magnetic coupler of backing carriage 206. After completing the full scan from the right end of substrate 212 to the left end, backing carriage 206 is stopped at the left end of backing rail 210, such that black backing surface 208B is positioned at the left end of substrate 212. Measurement carriage 202 travels further to the left in the direction of arrow 216 for decoupling from the black magnetic coupler and coupling to the white magnetic coupler, as depicted in FIG. 2D.

Color measurement system 200 is employed for acquiring color measurements of printed substrate 212 (e.g., measuring the opacity of a non-opaque printed substrate 212) via calculations made from at least two measurements. One measurement is made of a target area on the non-opaque printed substrate 212 backed by an appropriate white backing material (i.e., white backing surface 208W), and the other measurement of the same target area backed by an appropriate black backing material (i.e., black backing surface 208B). In the example of FIGS. 2A-2D, the described measurement sampling pattern is a full lateral movement across the width of the printed substrate with a white backing followed by a full lateral movement with a black backing. Alternatively, other measurements sampling patterns can be employed, for example, acquiring color measurement of each target area with a white backing and with a black backing before moving on to the next target area. For example, the decoupling of the magnetic coupler of measurement carriage 202 from one of the magnetic couplers of backing carriage can be done by turning off an electromagnet magnetic coupler.

Figure 3A:
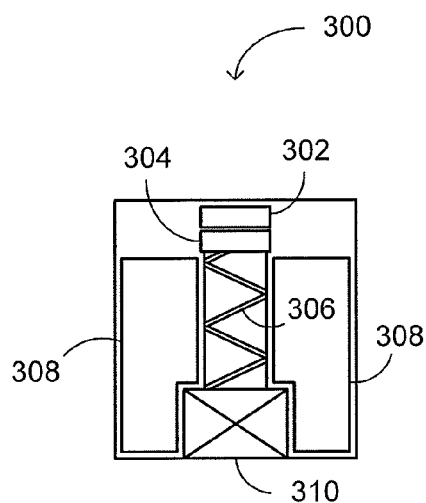
FIGS. 3A and 3B are schematic illustrations of a backing carriage, generally referenced 300, constructed and operative in accordance with a further embodiment of the disclosed technique.
Figure 3B:
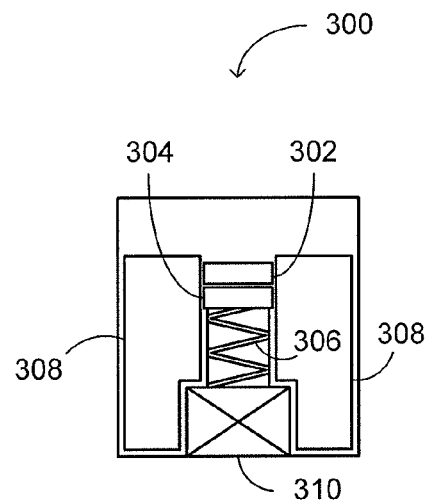

Reference is now made to FIGS. 3A and 3B, which are schematic illustrations of a backing carriage, generally referenced 300, constructed and operative in accordance with a further embodiment of the disclosed technique. With reference to FIG. 3A, backing carriage 300 is slidably mounted onto a backing rail 310. Backing carriage 300 is depicted from a front side view such that rail 310 extends perpendicularly to the image plane toward (or away from) the viewer. Backing carriage 300 includes a backing surface 302, a magnetic coupler 304, a retarding spring 306, and a dust barrier 308. Backing surface 302 and magnetic coupler 304 are both mounted on retarding spring 306. Dust barrier 308 surrounds rail 310.

Magnetic coupler 304 is magnetically coupled with a measurement magnetic coupler of a measurement carriage (both not shown—e.g., magnetic coupler 106 of measurement carriage 102 of FIGS. 1A and 1B), for coupling backing carriage 300 with the measurement carriage. The magnetic coupling enables backing carriage 300 to follow the (i.e., or to move in unison with) measurement carriage without having an autonomous motor. By controlling the force of the magnetic coupling and in accordance with the retarding force of retarding spring 306 the elevation of backing surface 302 is controlled. For example, in case magnetic coupler 304, the magnetic coupler of the measurement carriage (or both), is an electromagnet, by varying the strength of the electrical field of the electromagnet magnetic coupler, the relative position (i.e., elevation) of backing surface 302 is actively controlled. By controlling the elevation of backing surface 302 with respect to an inspected printed substrate (not shown—e.g., printed substrate 124 of FIGS. 1A and 1B), backing surface 302 can be moved to momentary contact the inspected substrate for modifying the nature of the measurement geometry. In the example set forth in FIG. 3A, the magnetic coupling force is stronger than in the example set forth in FIG. 3B, and therefore backing surface 302 as depicted in FIG. 3A is elevated higher than backing surface 302 as depicted in FIG. 3B. That is, backing surface 302 would be closer to the printed substrate in FIG. 3A than in FIG. 3B.

Dust barrier 308 can be formed of a bristles brush, a flexible membrane or any flexible sheet. Dust barrier 308 protects rail 310 from dust or other particles which might penetrate between backing carriage 300 and rail 310, thereby for example, increasing the friction between backing carriage 300 and rail 310. In addition dust barrier 308 also provides some motion damping to backing carriage 300 as it follows the measurement carriage, thereby enabling controlling the movement of backing carriage 300. For example, dust barrier 308 is employed for dampening oscillations of backing carriage 300 around the stopping point of the measurement carriage.

Figure 4:
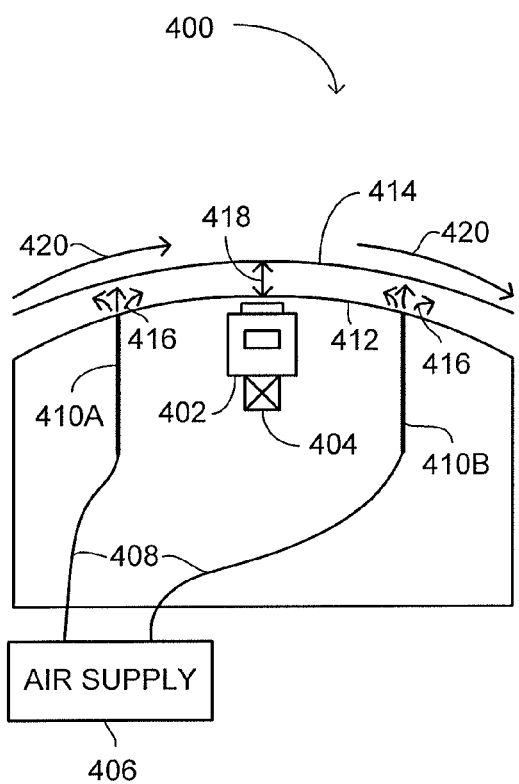
FIG. 4 is a schematic illustration of a laterally moving color measurement system for use with a printed material conveying apparatus (herein in referred to as simply a conveying apparatus), constructed and operative in accordance with another embodiment of the disclosed technique.

Reference is now made to FIG. 4, which is a schematic illustration of a laterally moving color measurement system for use with a printed material conveying apparatus (herein in referred to as simply a conveying apparatus), generally referenced 400, constructed and operative in accordance with another embodiment of the disclosed technique. Color measurement system 400 includes a measurement carriage mounted on a measurement rail (both not shown), a backing carriage 402 mounted on a backing rail 404, an air supply source 406, air conduits 408, two air knives 410A and 410B, and a curved upper surface 412. The measurement and backing carriages are similar in structure and operation to those described herein above with reference to FIGS. 1A-1B, 2A-2D and 3A-3D.

It is noted that color measurement system 400 may include only a single air knife (not shown) or a plurality of air knives (not shown). In a preferred embodiment of the disclosed technique, color measurement system 400 includes two air knives 410A and 410B. Air supply 406 is coupled with air knives 410A and 410B via air conduits 408. Air supply 406 supplies air to air knives 410A and air knife 410B. It is noted that the location of air knives 410A and 410B in FIG. 4 represent one possible positioning of the air knives on curved upper surface 412. Other configurations of the positioning of the air knives on or around curved upper surface 412 are possible and are a matter of design choice.

When air is supplied to at least one of air knives 410A or 410B, air is expelled to the outer surface of curved upper surface 412. This is shown schematically by a plurality of arrows 416. The expelled air generates an additional thin film of air which separates the outer surface of curved upper surface 412 from an object 414, such as a web substrate, which travels over curved upper surface 412, as shown by a plurality of arrows 420. The thin film of air naturally follows the shape of curved upper surface 412. The thin film of air can be defined by its thickness, or in other words, the distance between the outer surface of curved upper surface 412 and object 414. This is shown schematically in FIG. 4 by a double-headed arrow 418.

In general, Color measurement system 400 is coupled with a conveying apparatus (not shown), such as a printing press, for enabling chromatic characteristics of object 414 to be determined. As shown above in FIGS. 1A-1B and 2A-2D the measurement carriage of color measurement system 400 includes an optical sensor (not shown) and a light source (not shown).

As object 414 travels over curved upper surface 412, a thin film of air is self-generated due to the phenomenon of air entrainment. Air entrainment is exhibited when a moving surface of an object drags a thin layer of air next to the moving surface in the direction of motion of the moving surface. The phenomenon is due to the interaction of ambient air and the surface characteristics of object 414 as well as of curved upper surface 412 (such as surface roughness, flatness, porosity and the like). Furthermore, the thickness of the entrained air layer is additionally influenced by the velocity of object 414, the tension of object 414, the curvature of curved upper surface 412 and the wrap angle of object 414 over curved upper surface 412.

The thickness of the thin film of air can be monitored and controlled by a monitoring sensor (not shown) coupled with color measurement system 400. The monitoring sensor may be integrated into color measurement system 400, or may be mounted externally thereto, in such a position as to be able to detect the displacement between object 414 and curved upper surface 412. The monitoring sensor could be embodied, for example, as an ultrasonic sensor, an optical reflection sensor, a capacitive sensor and the like, and can be used to determine the displacement between object 414, as it is conveyed, and curved upper surface 412.

The underlying curvature of curved upper surface 412 determines to some extent the amount of entrained air which inherently flows over curved upper surface 412. The amount of entrained air determines the thickness (as shown by double-headed arrow 418) of the thin film of air in the absence of any supplemental air supplied by at least one of air knives 410A or 410B. The curvature of curved upper surface 412 can be determined based on known run conditions of the conveying apparatus coupled with color measurement system 400. The run conditions can include the velocity and tension of object 414 as it passes over curved upper surface 412. The run conditions can include other characteristics of object 414 and curved upper surface 412. This is described in the following articles: "Characteristics of Air Film Thickness and Flow Visualization for Transporting Film" to Aoki and Hashimoto, published in the Journal of Fluid Science and Technology, volume 5, number 3, 2010, pages 503-416, and "Air Film Thickness Estimation in Web Handling Processes" to Hashimoto, published in the Transactions of the ASME—Journal of Tribology, volume 121, January 1999, pages 50-55. It is noted that the curvature of upper curved surface 412 can be modeled after known curved surfaces, such as the one described in U.S. Pat. No. 4,956,737 to Brock, assigned to the Eastman Kodak Company. In addition, changing the velocity and volume of air flow of the air expelled from air knives 410A and 410B, including the possible use of negative air flow or vacuum, can affect the thickness of the thin film of air.

Backing rail 404 is positioned across a central portion (not referenced) of curved upper surface 412. Thus, backing carriage 402 mounted onto rail 404 runs across the central portion of curved upper surface. It is noted that the central portion of curved surface 412 is either transparent, or is completely removed, such that the light from the light source impinges on the backing surface (not shown) of backing carriage.

As mentioned above, the distance between curved upper surface 412 and object 414, as shown by double-headed arrow 418, is monitored. Any changes in the thickness of the thin film (arrow 418) may result in a change of the position of the optical detector, of the backing surface (e.g., as described in FIGS. 3A and 3B) or of both. Thereby, the distance between the detector, object 414 and the backing surface remains substantially constant, or at least within a predefined tolerance range. An actuator (not shown) coupled with the optical detector and with the monitoring sensor may be used to rapidly change the position of the optical detector in correspondence to changes in the thickness of the thin film. According to another embodiment of the disclosed technique, the distance between the optical detector and object 414 may be kept substantially constant or at least within a predefined tolerance range by physically moving color measurement system 400 towards or away from object 414. According to a further embodiment, this maintenance of the thickness of the thin film of air can be achieved by modifying the air velocity and the volume of the air expelled, or extracted from air knives 410A and 410B which affects the thickness of the thin film of air. It is also noted that a static separation (not shown) between the outer surface of curved upper surface 412 and object 414 may be achieved by at least one embossed section (not shown) on the outer surface of curved upper surface 412, by scarifying the edges of the outer surface of curved upper surface 412 or by scarifying a particular portion of the outer surface of curved upper surface 412.

It is noted that the backing surfaces of backing carriage 402 never come into contact with object 414, even if air supply 406 is turned off (or if air is extracted) and no thin film of air is present at the outer surface of curved upper surface 412. Thereby, the backing surfaces are protected and are not worn down by the conveyed object 414. It is also noted that curved surface 412 may have a different shape than the shape shown in FIG. 4. For example, curved surface 412 may have a rectangular shape.

It will be appreciated by persons skilled in the art that the disclosed technique is not limited to what has been particularly shown and described hereinabove. Rather the scope of the disclosed technique is defined only by the claims, which follow.

The invention claimed is:

1. A color measurement system for laterally determining the chromatic characteristics of a printed substrate conveyed by a conveying apparatus, the system comprising:

a measurement carriage including a measurement head for laterally moving across the width of said printed substrate and a measurement magnetic coupler, said measurement carriage slidably mounted onto a measurement rail positioned on a first side of said printed substrate; and a backing carriage including at least one backing surface and at least one backing magnetic coupler, each of said at least one backing magnetic coupler being associated with a respective one of said backing surface, each of said at least one backing magnetic coupler can be coupled with said measurement magnetic coupler for coupling said measurement carriage with said backing carriage, said backing carriage slidably mounted onto a backing rail positioned on a second side of said printed substrate, opposite said first side, wherein a selected one of said measurement carriage and said backing carriage including a motor for moving across a respective one of said measurement rail and said backing rail, and wherein another one of said measurement carriage and said backing carriage being moved across another one of said measurement rail and said backing rail by being coupled with said first one of said measurement carriage and said backing carriage.

2. The system of claim 1, wherein said at least one backing surface includes a white backing surface and a black backing surface.

3. The system of claim 1, wherein said measurement rail enables said measurement carriage to be decoupled from a selected one of said at least one backing magnetic coupler and be coupled with another one of said at least one backing magnetic coupler.

4. The system of claim 1, wherein said backing carriage further includes a retarding spring, said at least one backing surface being mounted onto said retarding spring, and wherein the force of the magnetic coupling between said measurement magnetic coupler and said at least one backing magnetic coupler being controlled, such that the elevation of said at least one backing surface being controlled.

5. The system of claim 1, further comprising an air supply source, air conduits, and at least one air knife, said air supply unit supplying pressurized air to said at least one air knife via said air conduits, said air knife being positioned below said printed substrate and expels the pressurized air for pushing said printed substrate, thereby preventing said printed substrate from coming into direct contact with said at least one backing surface.

6. The system of claim 1, wherein either one of said measurement magnetic coupler and said at least one backing magnetic coupler can be selected from the list consisting of:
a magnet;
a paramagnetic magnetic material;
a ferromagnetic magnetic material; and
an electromagnet.

* * * * *